(12) United States Patent
Zou et al.

(10) Patent No.: US 11,534,133 B2
(45) Date of Patent: Dec. 27, 2022

(54) ULTRASONIC DETECTION METHOD AND ULTRASONIC IMAGING SYSTEM FOR FETAL HEART

(71) Applicant: SHENZHEN MINDRAY BIO-MEDICAL ELECTRONICS CO., LTD., Guangdong (CN)

(72) Inventors: Yaoxian Zou, Shenzhen (CN); Muqing Lin, Shenzhen (CN); Yong Huang, Shenzhen (CN); Zhijie Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 16/608,675

(22) PCT Filed: Apr. 27, 2017

(86) PCT No.: PCT/CN2017/082246
§ 371 (c)(1),
(2) Date: Mar. 6, 2020

(87) PCT Pub. No.: WO2018/195874
PCT Pub. Date: Nov. 1, 2018

(65) Prior Publication Data
US 2020/0205772 A1     Jul. 2, 2020

(51) Int. Cl.
*A61B 8/08*    (2006.01)
*A61B 8/00*    (2006.01)

(52) U.S. Cl.
CPC ............ *A61B 8/0866* (2013.01); *A61B 8/085* (2013.01); *A61B 8/0883* (2013.01); *A61B 8/466* (2013.01); *A61B 8/523* (2013.01)

(58) Field of Classification Search
CPC ..... A61B 8/085; A61B 8/0866; A61B 8/0883; A61B 8/466; A61B 8/523
See application file for complete search history.

(56) References Cited

U.S. PATENT DOCUMENTS 8,083,678 B2 * 12/2011 Abuhamad ............ A61B 8/523
600/443
9,332,965 B2 * 5/2016 Lee ..................... G01S 7/52074
(Continued)

FOREIGN PATENT DOCUMENTS

CN     101184428 A    5/2008
CN     101739880 A    6/2010
(Continued)

OTHER PUBLICATIONS

PCT International Search Report and the Written Opinion dated Jan. 29, 2018, issued in related International Application No. PCT/CN2017/082246, with English machine translation (14 pages).

(Continued)

*Primary Examiner* — Angela M Hoffa
(74) *Attorney, Agent, or Firm* — Sheppard Mullin Richter & Hampton LLP

(57) ABSTRACT

An ultrasonic detection method and ultrasonic imaging system for a fetal heart. Since after three-dimensional volume data is obtained, at least one point within a fetal heart in the three-dimensional volume data is identified, the spatial position where a fetal heart cross-section is located in the three-dimensional volume data is identified according to the point, and the fetal heart cross-section is then extracted from the three-dimensional volume data according to the identified spatial position, the fetal heart cross-section can be quickly acquired from the three-dimensional volume data. The present invention is simple and easy to use, and is convenient for a doctor to make a diagnosis.

22 Claims, 4 Drawing Sheets

(56) References Cited

U.S. PATENT DOCUMENTS

| | | | |
|---|---|---|---|
| 10,582,912 B2* | 3/2020 | Yoo | A61B 8/14 |
| 11,039,810 B2 | 6/2021 | Zou et al. | |
| 11,229,419 B2 | 1/2022 | Zou et al. | |
| 2005/0004465 A1* | 1/2005 | Abuhamad | A61B 8/14 600/443 |
| 2005/0251036 A1* | 11/2005 | Abuhamad | A61B 8/463 600/437 |
| 2006/0241461 A1 | 10/2006 | White et al. | |
| 2011/0201935 A1 | 8/2011 | Collet-Billon et al. | |
| 2014/0050381 A1* | 2/2014 | Lee | A61B 8/465 382/131 |
| 2016/0038125 A1* | 2/2016 | Haas | A61B 8/483 600/440 |
| 2016/0098832 A1 | 4/2016 | Yoo et al. | |
| 2016/0249885 A1 | 9/2016 | Schneider et al. | |
| 2017/0007209 A1* | 1/2017 | Yoo | G06T 7/0012 |

FOREIGN PATENT DOCUMENTS

| | | | |
|---|---|---|---|
| CN | 102197316 A | 9/2011 |
| CN | 103927559 A | 7/2014 |
| CN | 103932741 A | 7/2014 |
| CN | 103955698 A | 7/2014 |
| CN | 104414680 A | 3/2015 |
| CN | 104680481 A | 6/2015 |
| CN | 105900140 A | 8/2016 |
| CN | 106102585 A | 11/2016 |
| CN | 106510759 A | 3/2017 |
| EP | 1681020 A1 | 7/2006 |

OTHER PUBLICATIONS

PCT International Preliminary Report on Patentability dated Nov. 7, 2019, issued in related International Application No. PCT/CN2017/082246, with English machine translation (11 pages).

PCT International Search Report and the Written Opinion dated Jan. 29, 2018, issued in related International Application No. PCT/CN2017/082246 (10 pages).

First Search dated May 23, 2021, issued in related Chinese Application No. 201780079230.3 (1 page).

First Office Action dated Jun. 1, 2021, issued in related Chinese Application No. 201780079230.3, with English machine translation (18 pages).

PCT International Preliminary Report on Patentability dated Nov. 7, 2019, issued in related International Application No. PCT/CN2017/082246, with English translation (11 pages).

Supplementary Search dated May 20, 2022, issued in related Chinese Application No. 201780079230.3 (3 pages).

* cited by examiner

ULTRASONIC DETECTION METHOD AND ULTRASONIC IMAGING SYSTEM FOR FETAL HEART

CROSS-REFERENCE TO RELATED PATENT APPLICATION

This application is a U.S. National Stage Application under 35 U.S.C. 371 of International Application No. PCT/CN2017/082246, filed on Apr. 27, 2017, the contents of which is incorporated herein by reference in its entirety in the present disclosure.

TECHNICAL FIELD

The present disclosure relates to ultrasound imaging, in particular to an ultrasound detection method and an ultrasound imaging system for fetal heart.

BACKGROUND

Ultrasound devices are generally used by a doctor to observe the internal tissues of a human body. The doctor may place an ultrasound probe on the surface of the skin corresponding to the human tissue to obtain an ultrasound image of that tissue. Because of its characteristics of safety, convenience, non-destructiveness, and low cost, etc., ultrasound imaging has become one of the main aids for the doctor to diagnose.

Obstetrics is one of the fields where ultrasound diagnosis is most widely used. In this field, because the ultrasound avoids the effects of X-rays or the like on the mother and the fetus, its application value is significantly superior to other imaging equipments. Specifically, ultrasound can not only observe and measure the morphology of the fetus, but also obtain a variety of physiological and case information such as fetal breathing and urinary, so as to evaluate the health and development status of the fetus. In an obstetric examination, the fetal heart is the focus and difficulty of the ultrasound examination. The reason is that the fetal heart is relatively small and has many cross-sections. These cross-sections are located in multiple positions of the fetal heart. The doctor can obtain the cross-section images of the fetal heart from different directions only after long period of training, and the examination process will take a long time. Commonly used cross-sections include four-chamber cardiac cross-section, left ventricular outflow cross-section, right ventricular outflow cross-section, aortic arch cross-section, aortic arch cross-section, three-vessel tracheal cross-section, gastric vesicle cross-section, five-chamber cardiac cross-section, and superior vena cava cross-section.

In recent years, three-dimensional ultrasound imaging has been widely used in clinical practice. The reason is that the three-dimensional ultrasound imaging can completely scan the tissue or organ to be detected at one time, and then the doctor can obtain the clinically required cross-section images through post-processing such as rotation and translation, etc., which greatly reduces the time for doctors to scan, and also facilitates data storage which facilitates the trace when problems are found later. For example, STIC (Spatiotemporal Image Correlation) technology scans the fetal heart once and then reorganizes the scan data into multi-volume data according to the cardiac cycle, which can enable the doctor to dynamically observe the movement of the fetal heart in three dimensions.

However, finding out the cross-section images in 3D space is not easy. The doctor needs to have a very deep understanding to 3D space to be able to find out the cross-section image through manual rotation and translation operations in three-dimensional. However, most ultrasound doctors have no technical background, and are lack of understanding to three-dimensional space. Therefore, it is very difficult for them to manually find out the median sagittal cross-section image from a volume data.

It is usually necessary to enter 7 points in 4 cross-section images in the 3D volume data, and then semi-automatically generate the cross-section image of the fetal heart. Although this method can obtain the cross-section image of the fetal heart, the operation is tedious and requires high professional quality of the doctor, and it is very difficult to be promoted in clinical practice. Therefore, it is desired to further improve the acquisition method of the fetal heart cross-section image in the ultrasound device.

SUMMARY

The invention provides a fetal heart ultrasound detection method and an ultrasound imaging system, which can automatically or manually identify at least one point in the fetal heart in three-dimensional volume data, and automatically generate a series of standard fetal heart cut planes based on the point.

According to a first aspect, in one embodiment, an ultrasound detection method for a fetal heart is provided, which may include:

transmitting ultrasound waves to a tissue containing the fetal heart;

receiving ultrasound echoes to obtain ultrasound echo signals;

obtaining a three-dimensional volume data according to the ultrasound echo signals;

identifying at least one point in the fetal heart in the three-dimensional volume data;

identifying a spatial position of a cross-section of the fetal heart in the three-dimensional volume data according to the point;

obtaining an image of the cross-section of the fetal heart from the three-dimensional volume data according to the identified spatial position; and displaying the image of the cross-section of the fetal heart.

In one embodiment, the point may at least include an arbitrary point in a heart valve, a ventricular septum, an atrial septum, a left ventricle, a right ventricle, a left atrium, a right atrium, a gastric vesicle, a superior vena cava, a inferior vena cava, a pulmonary artery, an aorta, an aortic arch, a descending aorta, a four-chamber heart intersection or a spine.

In one embodiment, identifying the at least one point in the fetal heart in the three-dimensional volume data may include:

displaying an ultrasound image, where the ultrasound image is a two-dimensional section image and/or a three-dimensional image in the three-dimensional volume data; and obtaining a point inputted by an user on the ultrasound image as the point.

In one embodiment, identifying the at least one point in the fetal heart in the three-dimensional volume data may further include:

providing an auxiliary icon for displaying a positional relationship between a cross-section and a point, so as to prompt the user to input the point on the ultrasound image.

In one embodiment, identifying the at least one point in the fetal heart in the three-dimensional volume data may include automatically identifying the at least one point in the fetal heart in the three-dimensional volume data according to a characteristics of an anatomical structure of the fetal heart.

In one embodiment, identifying the spatial position of the cross-section of the fetal heart in the three-dimensional volume data according to the point may include:

searching for an anatomical structure near the point;

identifying a target area from the anatomical structure; and identifying the spatial position of the cross-section of the fetal heart in the three-dimensional volume data according to the target area.

In one embodiment, the target area comprises at least one of a heart valve, a ventricular septum, an atrial septum, a left ventricle, a right ventricle, a left atrium, a right atrium, a gastric vesicle, a superior vena cava, an inferior vena cava, a pulmonary artery, an aorta, an aortic arch, a descending aorta and a spine.

In one embodiment, an annotation may be performed on the displayed image of the cross-section of the fetal heart.

In one embodiment, the ultrasound detection method for the fetal heart may further include displaying an ultrasound image, where, the ultrasound image is a two-dimensional section image and/or a three-dimensional image in the three-dimensional volume data, and when ultrasound images that changes over time are displayed, the displayed image of the cross-section of the fetal heart also changes over time.

According to a second aspect, in one embodiment, an ultrasound imaging system is provided, which may include:

an ultrasound probe;

a transmitting/receiving control circuit which is configured to control the ultrasound probe to transmit ultrasound waves to a tissue containing a fetal heart and receive ultrasound echoes to obtain ultrasound echo signals;

a data processor which is configured to obtain a three-dimensional volume data according to the ultrasound echo signals, identify at least one point in the fetal heart in the three-dimensional volume data, identify a spatial position of a cross-section of the fetal heart in the three-dimensional volume data according to the point and obtain an image of the cross-section of the fetal heart from the three-dimensional volume data according to the identified spatial position; and a display which is configured to display the image of the cross-section of the fetal heart.

In one embodiment, the point may at least include an arbitrary point in a heart valve, a ventricular septum, an atrial septum, a left ventricle, a right ventricle, a left atrium, a right atrium, a gastric vesicle, a superior vena cava, a inferior vena cava, a pulmonary artery, an aorta, an aortic arch, a descending aorta, a four-chamber heart intersection or a spine.

In one embodiment, the ultrasound imaging system may further include an input device which is configured to obtain a point inputted by an user on an ultrasound image and send the point to the data processor as the point, where the ultrasound image is a two-dimensional section image and/or a three-dimensional image in the three-dimensional volume data and is generated by the data processor according to the ultrasound echo signals and displayed by the display.

In one embodiment, the display may further be configured to provide an auxiliary icon for displaying a positional relationship between a section and a point, so as to prompt the user to input the point on the ultrasound image.

In one embodiment, the data processor may be configured to automatically identify the at least one point in the fetal heart in the three-dimensional volume data according to a characteristics of an anatomical structure of the fetal heart.

In one embodiment, the data processor may be configured to search for an anatomical structure near the point, identify a target area from the anatomical structure, and identify the spatial position of the cross-section of the fetal heart in the three-dimensional volume data according to the target area.

In one embodiment, the target area may include at least one of a heart valve, a ventricular septum, an atrial septum, a left ventricle, a right ventricle, a left atrium, a right atrium, a gastric vesicle, a superior vena cava, an inferior vena cava, a pulmonary artery, an aorta, an aortic arch, a descending aorta and a spine.

In one embodiment, the display may further be configured to perform an annotation on the displayed image of the cross-section of the fetal heart.

In one embodiment, the display may further be configured to display an ultrasound image, and when ultrasound images that changes over time are displayed, the displayed image of the cross-section of the fetal heart also changes over time, where the ultrasound image may be a two-dimensional section image and/or a three-dimensional image in the three-dimensional volume data and is generated by the data processor according to the ultrasound echo signals.

In the ultrasound detection methods and the ultrasound imaging systems for fetal heart of the embodiments above, after obtaining the three-dimensional volume data, at least one point in the fetal heart in the three-dimensional volume data may be identified, the spatial position of the cross-section of the fetal heart in the three-dimensional volume data may be identified according to the point, and the image of the cross-section of the fetal heart may be obtained from the three-dimensional volume data according to the identified spatial position. Thereby, the image of the cross-section of the fetal heart can be quickly obtained from the three-dimensional volume data, which is simple and easy to use, and very convenient for doctors to diagnose.

DETAILED DESCRIPTION

Figure 1:
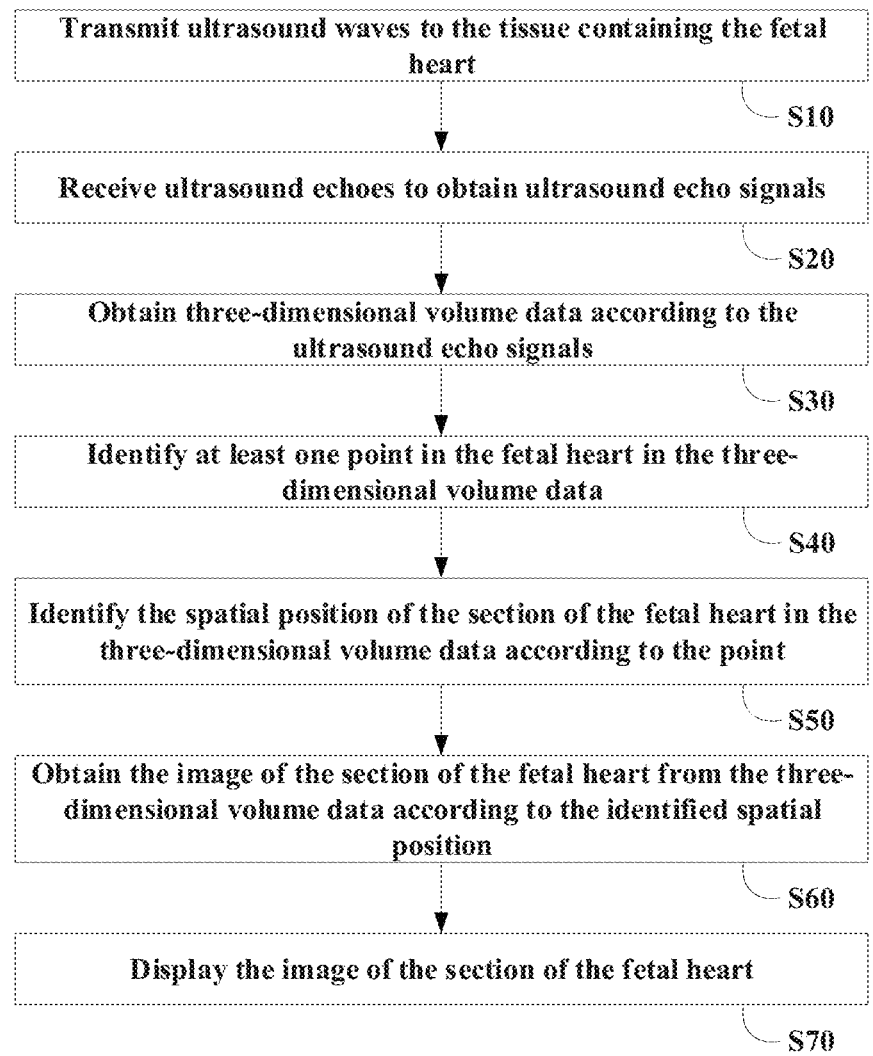
FIG. 1 is a flowchart of an ultrasound detection method for fetal heart according to one embodiment.

The present disclosure will be further described in detail below through specific embodiments in connection with the drawings. In different embodiments, similar elements are designated with associated similar numbers. In the following embodiments, many details are described so that the present application can be better understood. However, those skilled in the art can easily realize that some of the features may be omitted in different situations, or may be replaced by other elements, materials or methods. In some cases, certain related operations of the present disclosure are not shown or described in the description, which is to avoid that the core part of the present disclosure is overwhelmed by too much description. For those skilled in the art, detailed description of the related operations is not necessary. They can fully understand the related operations according to the description of the present disclosure and the general technical knowledge in the field.

In addition, the characteristics, operations or features described in the present disclosure may be combined in any suitable manner to form various embodiments. Furthermore, the steps or actions described in the method may also be changed or adjusted in the execution order in a manner obvious to those skilled in the art. Therefore, the orders in the description and drawings are only for clearly describing a certain embodiment, but not meant to be a necessary order, unless it is otherwise stated that a certain order must be followed.

The serial numbers of the components in the present disclosure, such as "first", "second", etc., are only used to distinguish the objects to be described, and do not have any order or technical meaning. The terms "connection" and "coupling" in the present disclosure include direct and indirect connection (coupling) unless otherwise stated.

The present disclosure provides an ultrasound detection method for fetal heart and an ultrasound imaging system, in which at least one point in a fetal heart in acquired three-dimensional volume data may be automatically or manually identified, a spatial position of a cross-section of the fetal heart in the three-dimensional volume data may be identified according to the point, and an image of the cross-section of the fetal heart may be extracted from the three-dimensional volume data according to the identified spatial position. The inventive concept of the present disclosure will be described first below.

The clinical cross-section of a fetal heart usually refers to a cross-section where specific tissue structures are located. For example, in the four-chamber heart cross-section of a fetal heart, the left ventricle, the right ventricle, the left atrium, the right atrium, the descending aorta, the spine and other anatomical structures are located. Therefore, in order to detect a cross-section from a three-dimensional volume data, it may be desired to identify the spatial positions of certain important anatomical structures located in the cross-section in the three-dimensional volume data. The inventors consider to identify an arbitrary point in an easy-to-recognize anatomical structure located in the cross-section, and then use this point to determine the spatial position of the cross-section of the fetal heart in the three-dimensional volume data, and thereafter obtain the image of the cross-section from the three-dimensional volume data according to the determined spatial position of the cross-section of the fetal heart in the three-dimensional volume data. The cross-sections of the fetal heart mentioned herein may include at least one of four-chamber heart cross-section, left ventricular outflow cross-section, right ventricular outflow cross-section, arterial catheter arch cross-section, aortic arch cross-section, three-vessel tracheal cross-section, gastric vesicle cross-section, five-chamber heart cross-section, and the superior vena cava cross-section, etc. The spatial position may usually be expressed by coordinates in a three-dimensional spatial coordinate system. The spatial position records the orientation of the cross-section in three-dimensional space.

Embodiment 1

Referring to FIG. 1, in one embodiment of the present disclosure, an ultrasound detection method for fetal heart is provided, which may include steps S10 to S70.

In step S10, ultrasound waves may be transmitted to a tissue containing a fetal heart with an ultrasound probe.

In step S20, ultrasound echoes may be received to obtain ultrasound echo signals.

In step S30, a three-dimensional volume data may be obtained according to the ultrasound echo signals. The ultrasound probe herein may be a one-dimensional probe or a two-dimensional array probe. The three-dimensional volume data may be a volume data obtained by the two-dimensional array probe, or a three-dimensional volume data obtained by performing a three-dimensional reconstruction on multiple frames of two-dimensional ultrasound images obtained by other types of probes, or a data acquired by STIC (Spatiotemporal Image Correlation) technology or one or more volumes of three-dimensional volume data from a four-dimensional ultrasound data.

In step S40, at least one point in the fetal heart in the three-dimensional volume data may be identified. In order to improve the identification accuracy, the point may be certain points of the tissue structure that can be easily identified in the anatomical structure in the three-dimensional volume data. For example, in one embodiment, the point may at least include an arbitrary point on the heart valve, the ventricular septum, the atrial septum, the left ventricle, the right ventricle, the left atrium, the right atrium, the gastric vesicle, the superior vena cava, the inferior vena cava, the pulmonary artery, the aorta, the aortic arch, the descending aorta, the four-chamber heart intersection or the spine. In one embodiment, the point may include any one of the four-chamber heart intersection point, the center point of the left ventricle, the center point of the right ventricle, the center point of the left atrium, the center point of the right atrium, the center point of the gastric vesicle, the superior vena cava point, a point on the descending aorta and a point on the spine. The heart valve herein may include the atrioventricular valve (such as the mitral valve or the tricuspid valve), the venous valve, or the aortic valve, etc.

The at least one point in the fetal heart in the three-dimensional volume data identified in step S40 may be identified by the system automatically, or may be determined by an user input. In one embodiment, step S40 may include automatically identifying the at least one point in the fetal heart in the three-dimensional volume data according to the characteristics of the anatomical structure of the fetal heart. In one embodiment, automatically identifying the at least one point in the fetal heart in the three-dimensional volume data according to the characteristics of the anatomical structure of the fetal heart may include: automatically extracting at least one section image from the three-dimensional volume data, automatically obtaining an arbitrary point in the fetal heart from the at least one section image by matching with a fetal heart template image, and mapping the point into the three-dimensional volume data.

Figure 2:
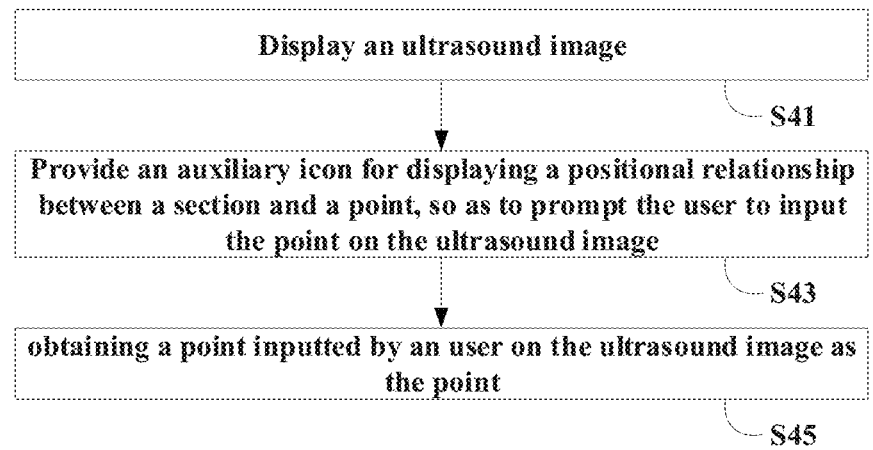
FIG. 2 is a flowchart for identifying at least one point in a fetal heart in a three-dimensional volume data in an ultrasound detection method for fetal heart in one embodiment.

Automatically identifying the point by the system is very convenient and fast. In another embodiment, in order to improve the accuracy of the identified point, the point may also be determined by user input. For example, in one embodiment, referring to FIG. 2, step S40 may include steps S41 to S45.

In step S41, the ultrasound image may be displayed. The ultrasound image may be a two-dimensional section image and/or a three-dimensional image in the three-dimensional volume data.

Figure 3:
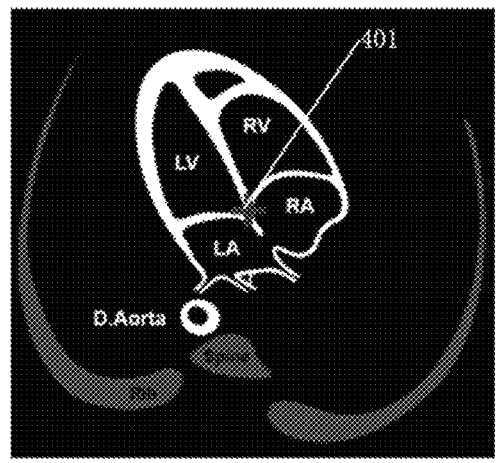
FIG. 3 is a schematic diagram of prompting a user to input a point on an ultrasound image in an ultrasound detection method for fetal heart in one embodiment.

In step S43, an auxiliary icon may be provided, which may display the positional relationship between the section and the point so as to prompt the user to input the point on the ultrasound image. Step S43 is not necessary, but it can guide the user to specify a point, which is easy to operate and very convenient and friendly to the user. For example, referring to FIG. 3, all sections and their points may be displayed by the auxiliary icons. The user may be prompted to designate the four-chamber heart intersection 401 as the point. In order to make the section more understandable, the anatomical structures in the section may be annotated with names or abbreviation of names.

In step S45, a point inputted by the user on the ultrasound image may be obtained as the point. Thereafter, in step S50, the spatial position of the cross-section of the fetal heart in the three-dimensional volume data may be automatically identified based on the point.

In one embodiment, the three-dimensional volume data used to identify the point in step S40 may be the data acquired by STIC (Spatiotemporal Image Correlation) technology or one volume of three-dimensional volume data in a four-dimensional ultrasound data.

Figure 4:
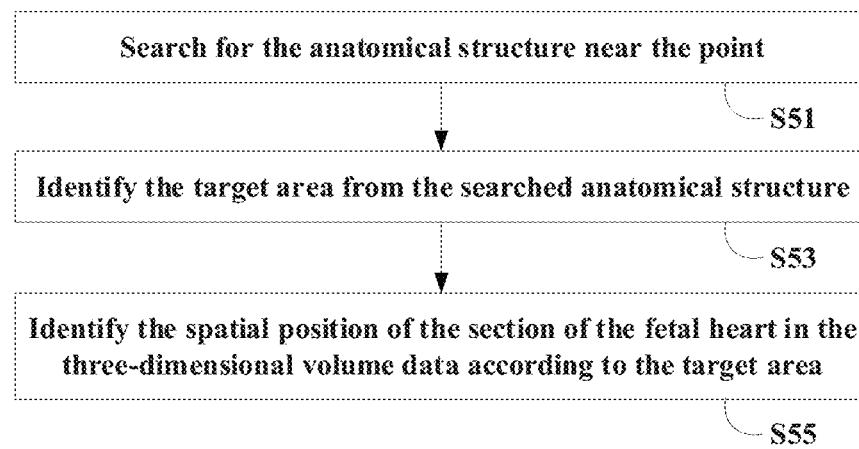
FIG. 4 is a flowchart of identifying a spatial position of a cross-section of a fetal heart in a three-dimensional volume data according to an obtained point in an ultrasound detection method for fetal heart in one embodiment.

In step S50, the spatial position of the cross-section of the fetal heart in the three-dimensional volume data may be identified according to the one or more points obtained in step S40. Taking the point being the four-chamber heart intersection as an example, after identifying the four-chamber heart intersection in the fetal heart in the three-dimensional volume data, the spatial position of the cross-section of the fetal heart in the three-dimensional volume data may be obtained according to the characteristics of the anatomical structures of the heart. In one embodiment, referring to FIG. 4, step S50 may include steps SM to S55.

In step SM, the anatomical structures near the point may be searched.

In step S53, a target area may be identified from the anatomical structure searched in step SM. In one embodiment, the target area may include at least one of a heart valve, a ventricular septum, an atrial septum, a left ventricle, a right ventricle, a left atrium, a right atrium, a gastric vesicle, a superior vena cava, an inferior vena cava, a pulmonary artery, an aorta, an aortic arch, a descending aorta and a spine.

Figure 5:
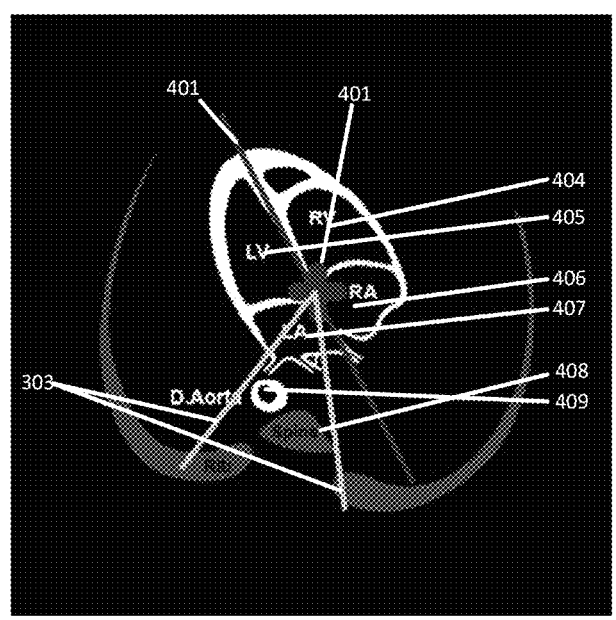
FIG. 5 is a schematic diagram of identifying a target area taking the case where a point is used as a four-chamber heart intersection as an example in an ultrasound detection method for fetal heart in one embodiment.

Still taking the point being the four-chamber heart intersection as an example, referring to FIG. 5, after identifying the point of the four-chamber heart intersection 401 in the fetal heart in the three-dimensional volume data, the long axis 402 of the heart may be identified from the three-dimensional volume data using straight line detection methods such as Hough transform or random Hough transform, etc. according to the spatial position of the four-chamber heart intersection 401 and the fact that the long axis of the heart will be represented as high echoes and approximately a straight line in the image; thereafter, the left ventricle 404, the right ventricle 405, the left atrium 406 and the right atrium 407 may be identified by segmenting the image using image segmentation methods or the like according to the spatial position of the long axis 402 of the heart in the three-dimensional volume data and the fact that the ventricle and the atrium will be represented as low echoes in the image. In addition, since the descending aorta and the spine are located below the left atrium, after obtaining the spatial positions of the four-chamber heart intersection 401 and the long axis 402 of the heart in the three-dimensional volume data, the spine 408 and/or the descending aorta 409 may be identified in an area at a certain angle to the four-chamber heart intersection 401 and the long axis 402 of the heart, such as the triangle area 403 in the figure. Specifically, since the spine will be represented as straight line-like high echoes in the image, the descending aorta will be represented as line-like low echoes in the image, and both will be represented as three-dimensional straight line-like structure in three-dimensional space, straight line detection methods in space may be used to identify the descending aorta and/or the spine to obtain the spatial positions of the descending aorta and/or the spine in the three-dimensional volume data.

Figure 6:
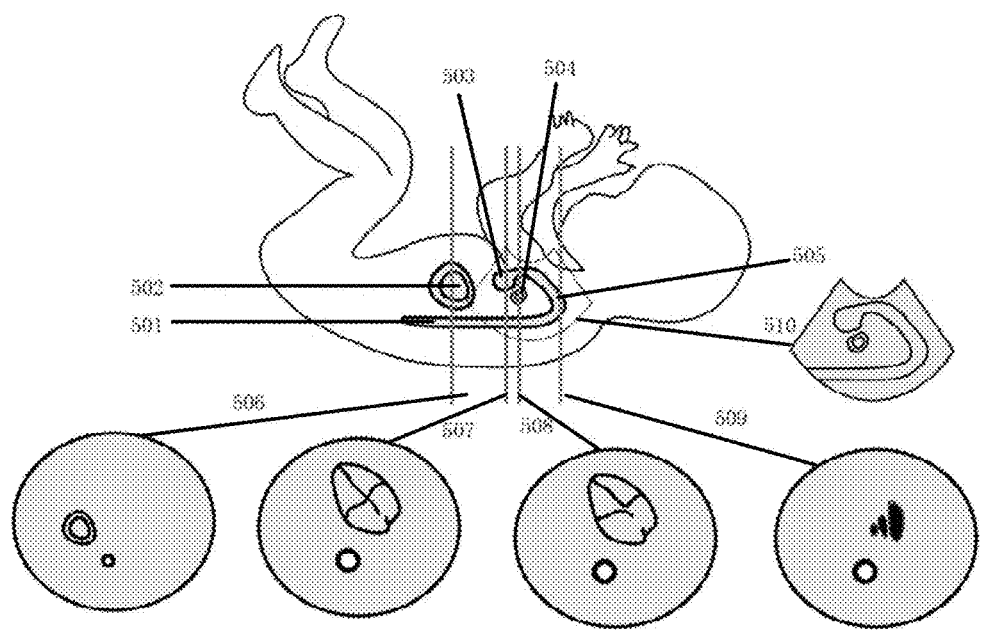
FIG. 6 is a schematic diagram of identifying a spatial position of a cross-section of a fetal heart in the three-dimensional volume data in an ultrasound detection method for fetal heart in one embodiment.

In step S55, the spatial position of the cross-section of the fetal heart in the three-dimensional volume data may be identified according to the target area. For example, still taking the point being the four-chamber heart intersection as an example, after identifying the four-chamber heart intersection, the left and right ventricles, the left and right atriums, the descending aorta and the spine in the three-dimensional volume data, the spatial position of the cross-section of the fetal heart in the three-dimensional volume data may be calculated according to their spatial positions in the three-dimensional volume data and the characteristics of the anatomical structures of the heart. For example, taking the target area being the descending aorta, the left and right ventricles and the left and right atriums as an examples, according to the characteristics of the anatomical structures of the heart, it will be known that the four-chamber heart section, the five-chamber heart section, the gastric vesicle section and the three-vessel trachea section are approximately perpendicular to the descending aorta in space; the right atrium is located above the aortic arch section and the long axis of the descending aorta is located below the aortic arch section; the right ventricle is located above the arterial catheter arch section and the long axis of the descending aorta is located below the arterial catheter arch section; the left ventricular outflow section includes the left ventricle and the descending aorta, etc.; the right ventricular outflow section is close to the arterial catheter arch section in space and includes the right ventricle, the aorta and the pulmonary artery; the superior vena cava section includes the right atrium and the superior and inferior vena cava; the gastric vesicle section is perpendicular to the descending aorta and is located below the four-chamber heart, and the distance of the gastric vesicle section to the four-chamber heart section may be roughly estimated based on empirical data which may be obtained according to the average value of a large amount of fetal data; and the aortic arch section may be extended from the center of the right atrium to the long axis of the descending aorta such that the right atrium and the long axis of the descending aorta are on the same section. Therefore, as shown in FIG. 6, according to the spatial positions of the descending aorta 501, the left and right ventricles and the left and right atriums in the three-dimensional volume data and the characteristics of the anatomical structure of the heart above, the spatial positions of the cross-sections in the three-dimensional volume data may be calculated, such as the gastric vesicle section 506, the four-chamber heart section 507, the five-chamber heart section 508, the three-vessel trachea section 509, and the arterial catheter arch section 510, etc. In FIG. 6, 502 indicates the gastric vesicle, 503 indicates the right ventricle, 504 indicates the aorta, and 505 indicates the pulmonary artery.

Multiple methods may be used to calculate the spatial positions of the cross-sections in the three-dimensional volume data according to the target area and the characteristics of the anatomical structure of the heart. For example, the principles of certain methods may be as below.

Mathematically, three non-collinear points in space will determine a plane, or a point and a direction of plane will determine a plane. Therefore, regarding a cross-section, its spatial position may be determined by obtaining the spatial positions of three points located in this cross-section or by obtaining the direction of, and the spatial position of a point located in, this cross-section. For example, regarding the four-chamber heart section, since the four-chamber heart section is perpendicular to the descending aorta, the spatial position of the four-chamber heart section may be determined according to the spatial position of the four-chamber heart intersection inputted by the user and the direction of the descending aorta. Regarding the gastric vesicle section, since the gastric vesicle section is perpendicular to the descending aorta, the spatial position of the gastric vesicle section may be determined according to the spatial position of the gastric vesicle and the direction of the descending aorta. Regarding the three-vessel trachea section, since the three-vessel trachea section is perpendicular to the descending aorta, the spatial position of the three-vessel trachea section may be determined according to the spatial position of the three-vessel trachea and the direction of the descending aorta. Regarding the arterial catheter arch section, since the right ventricle of the fetal heart will be displayed above the arterial catheter arch and the arterial catheter arch is located in the same section with the long axis of the descending aorta, the arterial catheter arch section may be determined according to the spatial positions of the right ventricle and the descending aorta. Other cross-sections may be determined by similar methods according to the corresponding anatomical structures.

It should be noted that, since the descending aorta and the spine are approximately parallel in space, in the methods of foregoing embodiments, the aorta may be replaced with the spine, or the descending aorta may be used in combination with the spine. It can be seen that, after the at least one point is determined, the spatial position of the cross-section of the fetal heart in the three-dimensional volume data may be obtained according to the anatomical position corresponding to the identified point and the image characteristics of at least one of the long axis of the heart, the spine and the descending aorta. The image characteristics may include the corresponding positional relationship of anatomical structures (such as the points, the long axis of the heart, the spine, and the descending aorta, etc.) in the image, and at least one of the shape of pixel area, the pixel value range, and image signal characteristics, etc. of the anatomical structures.

In the example shown in FIG. 6, the spatial position of the cross-section of the fetal heart in the three-dimensional volume data (hereinafter referred to as the coarsely positioned spatial position of the cross-section of the fetal heart) may be calculated according to the identified target area and the characteristics of the anatomical structures of the heart, but the characteristics of the anatomical structures of the heart are obtained according to prior knowledge, such as obtained by making statistics on the spatial relationships of the anatomical structures of many fetuses. However, there exists difference between the characteristics of the anatomical structure of the hearts of different individuals. Therefore, in order to improve the accuracy of the coarsely positioned spatial position of the cross-section of the fetal heart, the spatial position of the cross-section of the fetal heart in the three-dimensional volume data may be refined according to the characteristics of the three-dimensional volume data of the current fetus. There are many specific implementation methods. For example, corresponding algorithms may be designed according to the characteristics of the anatomical structures of the current fetus. For example, in the first method, since the gastric vesicles are usually represented as ellipsoidal objects with low or no echo in the volume image data of the fetal heart, the gastric vesicles may be segmented by image segmentation method. Specifically, a binary segmentation may be performed on the obtained three-dimensional volume data, and then certain morphological operations may be performed to obtain multiple candidate areas. Thereafter, the probability of the area being gastric vesicles may be determined for each candidate area based on characteristics such as shape, etc., and the area with the highest probability may be determined as the gastric vesicle area. For example, in the second method, certain special anatomical structures, such as the three-vessel trachea, etc., may also be detected in the obtained three-dimensional volume data using the template matching method. Specifically, three-vessel trachea data may be collected in advance to establish a template. During the detection, all possible areas in the three-dimensional volume data in the coarsely positioned range may be matched with the template to obtain the similarities, and the area with the highest similarity may be determined as the target area. For example, in the third method, certain special anatomical structures, such as the left ventricular outflow, may be detected from the three-dimensional volume data using a machine learning method. Specifically, a certain number of left ventricular outflow images, which are called positive samples, and a certain number of non-left ventricular outflow images, which are called negative samples, may be collected in advance. A machine learning algorithm may be designed to obtain, by automatic learning, features that can distinguish between the positive and negative samples. These features may be used to detect all possible areas in the three-dimensional volume data during the detection to obtain the probabilities that the areas are determined as the positive sample, and the area with the highest probability may be determined as the target area. Commonly used machine learning algorithms may include Adaboost algorithm, support vector machine (SVM), neural network algorithm, deep learning algorithm, etc. These algorithms may be used to automatically obtain the features that can distinguish the positive and negative samples.

In step S60, the image of the cross-section of the fetal heart may be obtained from the three-dimensional volume data according to the identified spatial position. In one embodiment, after the spatial position of the cross-section of the fetal heart in the three-dimensional volume data is identified, the spatial positions of other cross-sections may be further calculated according to the identified spatial position of such cross-section of the fetal heart, and the images of such other cross-sections may be obtained from the three-dimensional volume data according to the calculated spatial positions of such other cross-sections.

In step S70, the image of the cross-section of the fetal heart may be displayed. In one embodiment, when displaying the image of the cross-section of the fetal heart in step S70, if the ultrasound images that change over time are played, the displayed images of the cross-section of the fetal heart may also be changed over time. In one embodiment, in order to facilitate the user's observation, step S70 may further include performing annotations on the displayed image of the cross-section of the fetal heart so as to save time of the user (such as the doctor) for manual annotation. For example, the name, or abbreviation of the name, of the anatomical structure may be annotated on the image of the cross-section of the fetal heart.

Figure 9:
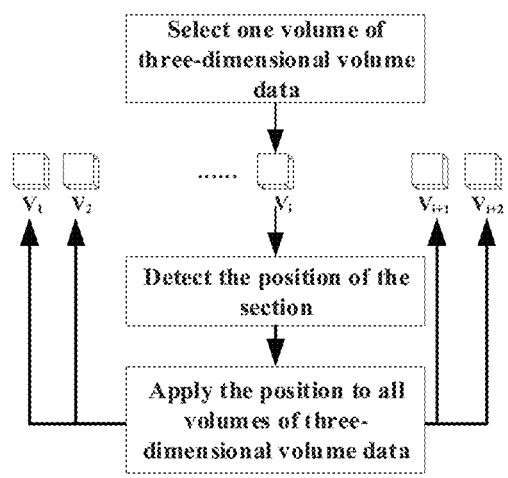
FIG. 9 is an example of section detection using multiple volumes of three-dimensional volume data in one embodiment.

In the identification of the at least one point in the fetal heart in the three-dimensional volume data and the identification of the spatial position of the cross-section of the fetal heart in the three-dimensional volume data according to the point in the step 40 and the step 50 above, the three-dimensional volume data may be STIC data or one volume of the three-dimensional volume data in a four-dimensional ultrasound data. As shown in FIG. 9, the point may be identified based on a volume of three-dimensional volume data Vi, and the spatial position of the cross-section of the fetal heart in the volume of three-dimensional volume data Vi may be detected based on the point. Thereafter, such spatial position may be applied to other volumes of three-dimensional volume data ($V_1, V_2, \ldots, V_{i+1}, V_{i+2}$), thereby achieving synchronously applying the position of the cross-section of the fetal heart identified in one volume of three-dimensional volume data to all three-dimensional volume data or to all three-dimensional volume data in a predetermined time period so as to reduce the amount of calculation and achieve the real-time tracking of changes in the cross-section of the fetal heart. In one embodiment, the processes of obtaining the image of the cross-section of the fetal heart from the three-dimensional volume data according to the identified spatial position and displaying the image of the cross-section of the fetal heart in the step 60 and the step 70 above may include:

obtaining the images of the cross-section of the fetal heart from multiple volumes of three-dimensional volume data based on the spatial position obtained according to the point identified in one volume of three-dimensional volume data, and displaying the images of the cross-section of the fetal heart obtained from the multiple volumes of three-dimensional volume data to show the changes of the images of the cross-section of the fetal heart. For example, the spatial position obtained according to the point identified in one volume of three-dimensional volume data may be applied to multiple volumes of three-dimensional volume data, and the images of the cross-section at such spatial position may be obtained from the multiple volumes of three-dimensional volume data as the images of the cross-section of the fetal heart for display. Therefore, as time passes, the change of the obtained image of the cross-section of the fetal heart over time may be shown, which facilitates the user to understand the results of the changes in the tissue in real time and can reduce the amount of calculation to improve the smoothness of image display.

Embodiment 2

Figure 7:
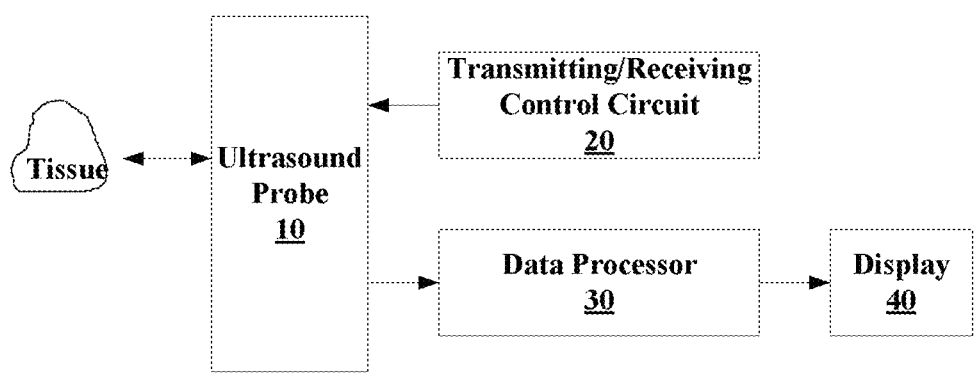
FIG. 7 is a schematic structural diagram of an ultrasound imaging system in one embodiment.

Referring to FIG. 7, in one embodiment of the present disclosure, an ultrasound imaging system is provided. The ultrasound imaging system may include an ultrasound probe 10, a transmitting/receiving control circuit 20, a data processor 30 and a display 40, which will be described in detail below.

The ultrasound probe 10 may include at least one transducer which may be configured to transmit an ultrasound wave according to an excitation electric signal outputted by the transmitting/receiving control circuit 20 or convert a received ultrasound wave into an electric signal. Therefore, each transducer may be used to transmit ultrasound waves to a target of interest in biological tissues, and may also be used to receive ultrasound echoes returned from the tissues. When performing ultrasound examination, a transmitting sequence and a receiving sequence may be used to control which transducers are used to transmit ultrasound waves and which transducers are used to receive ultrasound waves, or to control the transducers to transmit ultrasound waves or receive ultrasound echoes in time-sharing manner. The transducers to participate in ultrasound transmitting may be excited by electrical signals simultaneously, thereby transmitting ultrasound waves simultaneously. Alternatively, the transducers to participate in ultrasound transmitting may also be excited by multiple electrical signals with a certain time interval, thereby continuously transmitting ultrasound waves with a certain time interval.

The transmitting/receiving control circuit 20 may be used to control the ultrasound probe 10 to transmit an ultrasound beam to a biological tissue on the one hand, and control the ultrasound probe 10 to receive ultrasound echoes of the ultrasound beam reflected by the tissue on the other hand. In a specific embodiment, the transmitting/receiving control circuit 120 may be configured to generate a transmitting sequence and a receiving sequence. The transmitting sequence may be used to control a part or all of multiple transducers to transmit ultrasound waves to a target of interest in a biological tissue. The parameters of the transmitting sequence may include the number of the transducers used in the transmitting and the ultrasound transmitting parameters (such as amplitude, frequency, number of transmitting, transmitting interval, transmitting angle, wave pattern, etc.). The receiving sequence may be used to control a part or all of the multiple transducers to receive the ultrasound echoes reflected by the tissue. The parameters of the receiving sequence may include the number of the transducers used in the receiving and the receiving parameters of the echo (such as the receiving angle, depth, etc.). Depending on the application of the ultrasound echo or the images generated based on the ultrasound echo, the ultrasound parameters in the transmitting sequence and the echo parameters in the receiving sequence may also be different. In the embodiments of the present disclosure, the transmitting/receiving control circuit 20 may be configured to control the ultrasound probe 10 to transmit ultrasound waves to a tissue containing a fetal heart, and receive ultrasound echoes to obtain ultrasound echo signals.

The data processor 30 may be configured to obtain a three-dimensional volume data according to the ultrasound echo signals, identify at least one point in the fetal heart in the three-dimensional volume data, identify a spatial position of a cross-section of the fetal heart in the three-dimensional volume data according to the point, and obtaining an image of the cross-section of the fetal heart from the three-dimensional volume data according to the identified spatial position. In one embodiment, the point may at least include an arbitrary point in the heart valve, the ventricular septum, the atrial septum, the left ventricle, the right ventricle, the left atrium, the right atrium, the gastric vesicle, the superior vena cava, the inferior vena cava, the pulmonary artery, the aorta, the aortic arch, the descending aorta, the four-chamber heart intersection or the spine.

Figure 8:
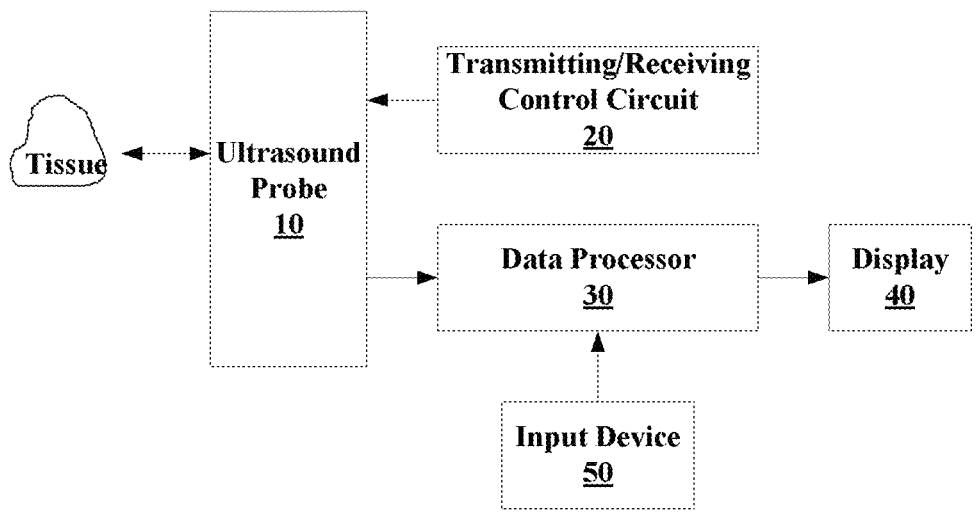
FIG. 8 is a schematic structural diagram of an ultrasound imaging system in another embodiment.

The at least one point in the fetal heart in the three-dimensional volume data may be automatically identified by the system. For example, in one embodiment, the data processor 30 may be configured to automatically identify at least one point in the fetal heart in the three-dimensional volume data according to the characteristics of the anatomical structures of the fetal heart. Automatically identifying the points is very convenient and quick. In order to improve the accuracy of the identified point, the point may also be determined by a user input. For example, in one embodiment, referring to FIG. 8, the ultrasound imaging system may further include an input device 50. The input device 50 may be configured to obtain a point inputted by the user on an ultrasound image and send it to the data processor 30 as the point, where the ultrasound image may be a two-dimensional section image and/or a three-dimensional image in the three-dimensional volume data, and may be generated by the data processor 30 according to the ultrasound echo signals and displayed by the display 40. In one embodiment, in order to guide the user to input the point, the display 40 may also be used to provide an auxiliary icon to show the position relationship of the section and the point, so as to prompt the user to input the point on the ultrasound image. The input device 50 may be a mouse, an input keyboard, or the like.

The data processor 30 may use various methods to identify the spatial position of the cross-section of the fetal heart in the three-dimensional volume data according to the point. For example, in one embodiment, the data processor 30 may search for an anatomical structure near the point, identify a target area from the searched anatomical structure, and identify the spatial position of the cross-section of the fetal heart in the three-dimensional volume data according to the target area. In one embodiment, the target area may include at least one of the heart valve, the ventricular septum, the atrial septum, the left ventricle, the right ventricle, the left atrium, the right atrium, the gastric vesicle, the superior vena cava, the inferior vena cava, the pulmonary artery, the aorta, the aortic arch, the descending aorta and the spine.

The display 40 may be used to display the obtained image of the cross-section of the fetal heart. In one embodiment, the display 40 may further be configured to perform annotation on the displayed image of the cross-section of the fetal heart, for example, annotating the name, or the abbreviation of the name, of the corresponding anatomical structure on the image of the cross-section of the fetal heart. In one embodiment, the display 40 may further be configured to display an ultrasound image. Furthermore, when the ultrasound images that change over time are played, the displayed image of the cross-section of the fetal heart may also change over time. The ultrasound image here may be a two-dimensional section image and/or a three-dimensional image in the three-dimensional volume data, which may be generated by the data processor according to the ultrasound echo signals. In one embodiment, the data processor may identify the spatial position of the cross-section of the fetal heart in the three-dimensional volume data according to the point by obtaining the spatial position of the cross-section of the fetal heart in the three-dimensional volume data according to the point and the image characteristics of at least one of the long axis of the heart, the spine and the descending aorta. For the specific description of the above steps, reference may be made to the description of the method steps in the foregoing embodiments, which will not be repeated here.

In one embodiment, in the process of identifying at least one point in the fetal heart in the three-dimensional volume data and identifying the spatial position of the cross-section of the fetal heart in the three-dimensional volume data according to the point, the three-dimensional volume data may be one volume of three-dimensional volume data, and, the data processor may obtain the image of the cross-section of the fetal heart from the three-dimensional volume data according to the identified spatial position and the display the image of the cross-section of the fetal heart by:

obtaining images of the cross-section of the fetal heart from multiple volumes of three-dimensional volume data according to the spatial position obtained based on the point identified in one volume of three-dimensional volume data; and displaying the images of the cross-section of the fetal heart obtained from the multiple volumes of three-dimensional volume data to show the changes in the cross-section of the fetal heart.

Regarding the specific implementation of the functions of the data processor in the present embodiment, reference may be made to the related description of step 10 to step 70 above, which will not be repeated here.

The present disclosure provides embodiments of ultrasound detection methods and ultrasound imaging systems for fetal heart above. In the embodiments, after obtaining three-dimensional volume data, at least one point in the fetal heart in the three-dimensional volume data may be identified, the spatial position of the cross-section of the fetal heart in the three-dimensional volume data may be identified according to the point, and the image of the cross-section of the fetal heart may be obtained from the three-dimensional volume data according to the identified spatial position. Therefore, with the present disclosure, the image of the cross-section of the fetal heart can be quickly obtained from the three-dimensional volume data, which is simple and easy to use, and very convenient for doctors to diagnose.

Specific examples are used to illustrate the present disclosure above. However, they are only used to facilitate the understanding to, but not intended to limit, the present disclosure. For those ordinarily skilled in the art, modifications may be made to the specific implementations according to the concepts of the present disclosure.

The invention claimed is:

1. An ultrasound detection method for a fetal heart, comprising:

transmitting ultrasound waves to a tissue containing the fetal heart;

receiving ultrasound echoes to obtain ultrasound echo signals;

obtaining a three-dimensional volume data according to the ultrasound echo signals;

identifying a single specific point directly from the three-dimensional volume data, wherein the single specific point is an arbitrary point in a heart valve, a ventricular septum, an atrial septum, a left ventricle, a right ventricle, a left atrium, a right atrium, a superior vena cava, an inferior vena cava, a pulmonary artery, an aorta, an aortic arch, a descending aorta, a four-chamber heart intersection, a center point of gastric vesicle, a superior vena cava point, a point on descending aorta, or a point on spine;

searching for an anatomical structure only near the single specific point;

identifying one or more target areas from the anatomical structure based on a relative positional relationship between the anatomical structure and the single specific point and image characteristics of the one or more target areas;

identifying a spatial position of a cross-section of the fetal heart in the three-dimensional volume data based on a spatial position of the single specific point and a direction of one identified target area or based on a spatial position of the single specific point and spatial positions of two identified target areas, wherein the cross-section is a four-chamber cardiac section, a left ventricular outflow section, a right ventricular outflow section, an aortic arch section, an aortic arch section, a three-vessel tracheal section, a five-chamber cardiac section, or a superior vena cava section;

obtaining an image of the cross-section of the fetal heart from the three-dimensional volume data according to the identified spatial position; and displaying the image of the cross-section of the fetal heart.

2. The method of claim 1, wherein the single specific point is a four-chamber heart intersection point, a center point of the left ventricle, a center point of the right ventricle, a center point of the left atrium, ora center point of the right atrium.

3. The method of claim 1, wherein identifying the single specific point directly from the three-dimensional volume data comprises:

displaying an ultrasound image, wherein the ultrasound image is a two-dimensional section image and/or a three-dimensional image in the three-dimensional volume data; and obtaining a point inputted by a user on the ultrasound image as the single specific point.

4. The method of claim 3, wherein identifying the single specific point directly from the three-dimensional volume data further comprises:

providing an auxiliary icon for displaying a positional relationship between a cross-section of the three-dimensional volume data and the single specific point, so as to prompt the user to input the inputted point on the ultrasound image.

5. The method of claim 1, wherein identifying the single specific point directly from the three-dimensional volume data comprises:

automatically identifying the single specific point directly from the three-dimensional volume data according to a characteristic of an anatomical structure of the fetal heart.

6. The method of claim 1, wherein the target area is a heart valve, a ventricular septum, an atrial septum, a left ventricle, a right ventricle, a left atrium, a right atrium, a gastric vesicle, a superior vena cava, an inferior vena cava, a pulmonary artery, an aorta, an aortic arch, a descending aorta or a spine.

7. The method of claim 1, further comprising: displaying an ultrasound image, wherein, the ultrasound image is a two-dimensional section image and/or a three-dimensional image in the three-dimensional volume data, and when ultrasound images that change over time are displayed, the displayed image of the cross-section of the fetal heart also changes over time.

8. The method of claim 1, wherein identifying the spatial position of the cross-section of the fetal heart in the three-dimensional volume data further comprises:

obtaining the spatial position of the cross-section of the fetal heart in the three-dimensional volume data according to the spatial position of each of the one or more target areas and image characteristics of at least one of a long axis of the heart, a spine and a descending aorta.

9. The method of claim 1, wherein the three-dimensional volume data is one volume of three-dimensional volume data, and obtaining the image of the cross-section of the fetal heart from the three-dimensional volume data according to the identified spatial position and displaying the image of the cross-section of the fetal heart comprises:

obtaining images of the cross-section of the fetal heart from multiple volumes of three-dimensional volume data based on the spatial position of each of the one or more target areas identified in the one volume of three-dimensional volume data; and displaying the images of the cross-section of the fetal heart obtained from the multiple volumes of three-dimensional volume data to show a change of the images of the cross-section of the fetal heart.

10. The method of claim 1, wherein identifying the spatial position of a cross-section of the fetal heart in the three-dimensional volume data comprises:

calculating a coarse position of the cross-section of the fetal heart in the three-dimensional volume data based on the spatial position of each of the one or more target areas and characteristics of anatomical structures of a heart; and refining the coarse position of the cross-section of the fetal heart in the three-dimensional volume data according to characteristics of the three-dimensional volume data of current fetus to obtain the spatial position of the cross-section of the fetal heart in the three-dimensional volume data.

11. The method of claim 1, wherein the image characteristics include a positional relationship of the anatomical structure in the image, and at least one of a shape of pixel area, a pixel value range, and image signal characteristics of the anatomical structure.

12. An ultrasound imaging system, comprising:

an ultrasound probe;

a transmitting/receiving control circuit configured to control the ultrasound probe to transmit ultrasound waves to a tissue containing a fetal heart and receive ultrasound echoes to obtain ultrasound echo signals;

a data processor configured to:

obtain a three-dimensional volume data according to the ultrasound echo signals, identify a single specific point directly from the three-dimensional volume data, wherein the single specific point is an arbitrary point in a heart valve, a ventricular septum, an atrial septum, a left ventricle, a right ventricle, a left atrium, a right atrium, a superior vena cava, an inferior vena cava, a pulmonary artery, an aorta, an aortic arch, a descending aorta, a four-chamber heart intersection, a center point of gastric vesicle, a superior vena cava point, a point on the descending aorta, or a point on spine, search for an anatomical structure only near the single specific point, identify one or more target areas from the anatomical structure based on a relative positional relationship between the anatomical structure and the single specific point and image characteristics of the one or more target areas, and identify a spatial position of a cross-section of the fetal heart in the three-dimensional volume data based on the spatial position of the single specific point and a direction of the identified one target area or based on the spatial position of the single specific point and the spatial positions of two of the identified target areas, wherein the cross-section is a four-chamber cardiac section, a left ventricular outflow section, a right ventricular outflow section, an aortic arch section, an aortic arch section, a three-vessel tracheal section, a five-chamber cardiac section, or a superior vena cava section; and a display configured to display the image of the cross-section of the fetal heart.

13. The ultrasound imaging system of claim 12, wherein the single specific point is a four-chamber heart intersection point, a center point of the left ventricle, a center point of the right ventricle, a center point of the left atrium, or a center point of the right atrium.

14. The ultrasound imaging system of claim 12, further comprising an input device configured to obtain a point inputted by a user on an ultrasound image and send the point to the data processor as the single specific point, wherein the ultrasound image is a two-dimensional section image and/or a three-dimensional image in the three-dimensional volume data, and is generated by the data processor according to the ultrasound echo signals and displayed by the display.

15. The ultrasound imaging system of claim 14, wherein the display is further configured to provide an auxiliary icon for displaying a positional relationship between a cross-section of the three-dimensional volume data and the single specific point, so as to prompt the user to input the single specific point on the ultrasound image.

16. The ultrasound imaging system of claim 12, wherein the data processor is configured to automatically identify the single specific point directly from the three-dimensional volume data according to a characteristic of an anatomical structure of the fetal heart.

17. The ultrasound imaging system of claim 12, wherein the target area is a heart valve, a ventricular septum, an atrial septum, a left ventricle, a right ventricle, a left atrium, a right atrium, a gastric vesicle, a superior vena cava, an inferior vena cava, a pulmonary artery, an aorta, an aortic arch, a descending aorta or a spine.

18. The ultrasound imaging system of claim 12, wherein, the display is further configured to display an ultrasound image, and when ultrasound images that change over time are displayed, the displayed image of the cross-section of the fetal heart also changes over time, wherein the ultrasound image is a two-dimensional section image and/or a three-dimensional image in the three-dimensional volume data and is generated by the data processor according to the ultrasound echo signals.

19. The ultrasound imaging system of claim 12, wherein the data processor identifies the spatial position of the cross-section of the fetal heart in the three-dimensional volume data further by:
obtaining the spatial position of the cross-section of the fetal heart in the three-dimensional volume data according to the spatial position of each of the one or more target areas and image characteristics of at least one of a long axis of the heart, a spine and a descending aorta.

20. The ultrasound imaging system of claim 12, wherein the three-dimensional volume data is one volume of three-dimensional volume data, and
the data processor obtains the image of the cross-section of the fetal heart from the three-dimensional volume data according to the identified spatial position and displaying the image of the cross-section of the fetal heart by:
obtaining images of the cross-section of the fetal heart from multiple volumes of three-dimensional volume data according to the spatial position of each of the one or more target areas identified in the one volume of three-dimensional volume data; and
displaying the images of the cross-section of the fetal heart obtained from the multiple volumes of three-dimensional volume data to show a change of the images of the cross-section of the fetal heart.

21. The ultrasound imaging system of claim 12, wherein the data processor identifies the spatial position of the cross-section of the fetal heart in the three-dimensional volume data by:
calculating a coarse position of the cross-section of the fetal heart in the three-dimensional volume data based on the spatial position of each of the one or more target areas and characteristics of anatomical structures of a heart; and
refining the coarse position of the cross-section of the fetal heart in the three-dimensional volume data according to characteristics of the three-dimensional volume data of current fetus to obtain the spatial position of the cross-section of the fetal heart in the three-dimensional volume data.

22. The ultrasound imaging system of claim 12, wherein the image characteristics include a positional relationship of the anatomical structure in the image, and at least one of a shape of pixel area, a pixel value range, and image signal characteristics of the anatomical structure.

* * * * *

UNITED STATES PATENT AND TRADEMARK OFFICE
CERTIFICATE OF CORRECTION

PATENT NO. : 11,534,133 B2
APPLICATION NO. : 16/608675
DATED : December 27, 2022
INVENTOR(S) : Yaoxian Zou et al.

Page 1 of 1

It is certified that error appears in the above-identified patent and that said Letters Patent is hereby corrected as shown below:

In the Claims

In Claim 13, Column 17, Lines 14-15, "right ventricle, a center point of the left atrium, ora center point of the right atrium" should read -- right ventricle, a center point of the left atrium, or a center point of the right atrium. --

Signed and Sealed this
Third Day of September, 2024

Katherine Kelly Vidal
*Director of the United States Patent and Trademark Office*